United States Patent
Fukuyori

(10) Patent No.: US 8,334,793 B2
(45) Date of Patent: Dec. 18, 2012

(54) SYSTEMS AND METHODS FOR INDEXING MEDIA FILES USING BRAINWAVE SIGNALS

(75) Inventor: Masahiro Fukuyori, Kawasaki (JP)

(73) Assignee: Fujitsu Limited, Kawasaki-shi (JP)

( * ) Notice: Subject to any disclaimer, the term of this patent is extended or adjusted under 35 U.S.C. 154(b) by 577 days.

(21) Appl. No.: 12/579,201

(22) Filed: Oct. 14, 2009

(65) Prior Publication Data

US 2011/0085780 A1    Apr. 14, 2011

(51) Int. Cl.
*H03M 11/00* (2006.01)

(52) U.S. Cl. .......................... 341/20; 600/545

(58) Field of Classification Search ............... 341/20; 600/544, 545, 300

See application file for complete search history.

(56) References Cited

U.S. PATENT DOCUMENTS

| | | | | |
|---|---|---|---|---|
| 5,983,129 A * | 11/1999 | Cowan et al. | ................. | 600/544 |
| 6,292,688 B1 * | 9/2001 | Patton | ........................... | 600/544 |
| 6,487,444 B2 * | 11/2002 | Mimura | ........................ | 600/544 |
| 7,761,144 B2 * | 7/2010 | Cox et al. | ....................... | 600/544 |
| 7,942,828 B2 * | 5/2011 | Teicher et al. | ................ | 600/558 |
| 8,157,609 B2 * | 4/2012 | Hallaian et al. | ............... | 446/173 |

\* cited by examiner

*Primary Examiner* — Brian Young
(74) *Attorney, Agent, or Firm* — Baker Botts L.L.P.

(57) ABSTRACT

A method may include selecting a media file and determining if the selected media file has been indexed. If the media file has not been indexed, the method may include playing the selected media file on a media device while simultaneously measure a brainwave signal of a user with a sensor, where the brainwave signal indicates an attention level of the user. Next, the method may include indexing the media file by correlating the measured brainwave signal to the media file and storing the media file and the measured brainwave signal in storage device.

14 Claims, 2 Drawing Sheets

SYSTEMS AND METHODS FOR INDEXING MEDIA FILES USING BRAINWAVE SIGNALS

TECHNICAL FIELD

The present disclosure relates to media processing, and in particular, systems and methods for indexing media files based at least on brainwave data.

BACKGROUND

Audio and/or visual data come from a variety of sources such as television broadcast, satellite broadcast, Internet-based broadcast, and radio broadcast and is steadily growing recently with the advancement of technology, especially in the field of consumer electronic products and broadband Internet access. In many cases, for example in broadcasting companies, multimedia libraries are so vast that an efficient indexing mechanism that allows for retrieval of specific footage is necessary. This indexing mechanism can be even more important when attempting to rapidly retrieve specific multimedia footage such as, for example, sports highlights or breaking news. Similarly, for Internet-based filing or even for a personal media collection, the ability to index a media file (e.g., funny or dramatic scenes of a video) is also needed.

Currently, a common method for generating an index of a media file includes manually entering indices, or tags, as the media file is being played. These tags are typically entered via an input device, such as a keyboard, and are often associated with the media's timeline. While effective, this post-processing of the multimedia footage can be extremely time-consuming and expensive.

SUMMARY

In accordance with embodiments of the present disclosure, a method for indexing media files is provided. The method may include receiving a selected a media file and playing the selected media file on a media device while simultaneously measuring a brainwave signal of a user with a sensor, where the brainwave signal indicates an attention level of the user. Next, the method may include indexing the media file by correlating the measured brainwave signal to the media file and storing the media file and the measured brainwave signal in storage device.

In accordance with some embodiments of the present disclosure, a system for indexing media files is provided. The system may include a media device, a sensor, a processor coupled to the sensor, and a storage device coupled to the processor. The media device may be configured to play a media file simultaneously with the measuring of brainwave signals of a user, wherein the brainwave signal indicates an attention level of the user by the sensor. The processor may be configured to receive the measured brainwave signals and index the media file by correlating the measured brainwave signal to the media file. The storage device may be configured to store the measured brainwave signal, the media file, and the correlation of the measured brainwave signal and the media file.

The system and method of the present disclosure provides technical advantages including, for example, automatic indexing of media files commonly found in a broad range of industries including, for example, broadcasting, Web-based media file sharing websites, journalism, audio books formats, etc. The system and method of the present disclosure may also provide automatic indexing for consumers looking to index a personal media collection, e.g., home videos, etc.

It will be understood that the various embodiments of the present invention may include some, all, or none of the enumerated technical advantages. In addition, other technical advantages of the present invention may be readily apparent to one skilled in the art from the figures, description and claims included herein.

BRIEF DESCRIPTION OF THE DRAWINGS

A more complete understanding of the present embodiments and advantages thereof may be acquired by referring to the following description taken in conjunction with the accompanying drawings, in which like reference numbers indicate like features, and wherein.

DETAILED DESCRIPTION

Figure 1:
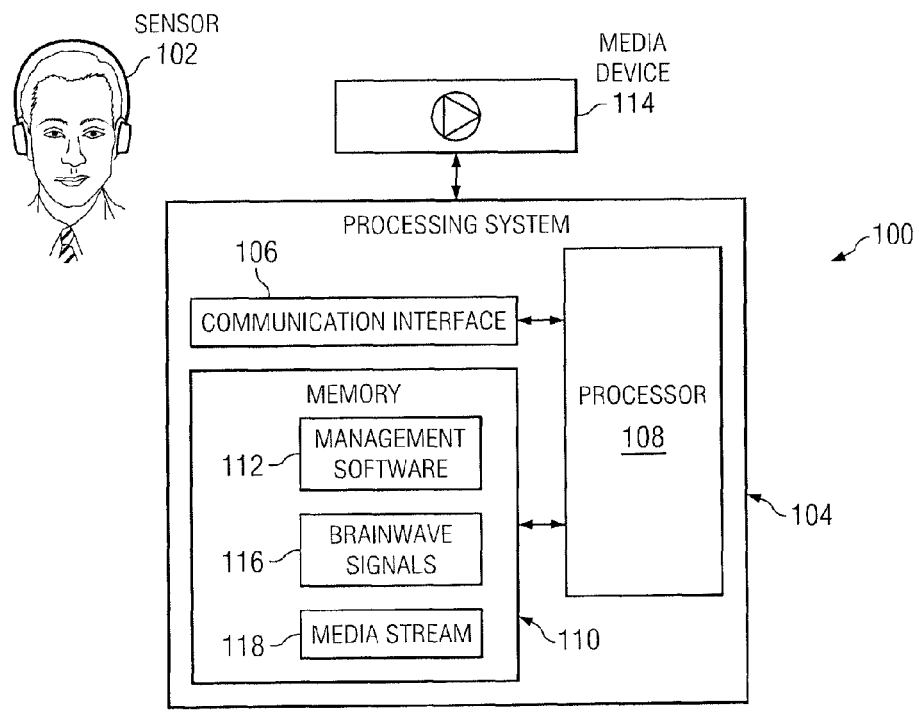
FIG. 1 illustrates an example system for indexing media files based on brainwave data, in accordance with particular embodiments of the present disclosure.
Figure 3:
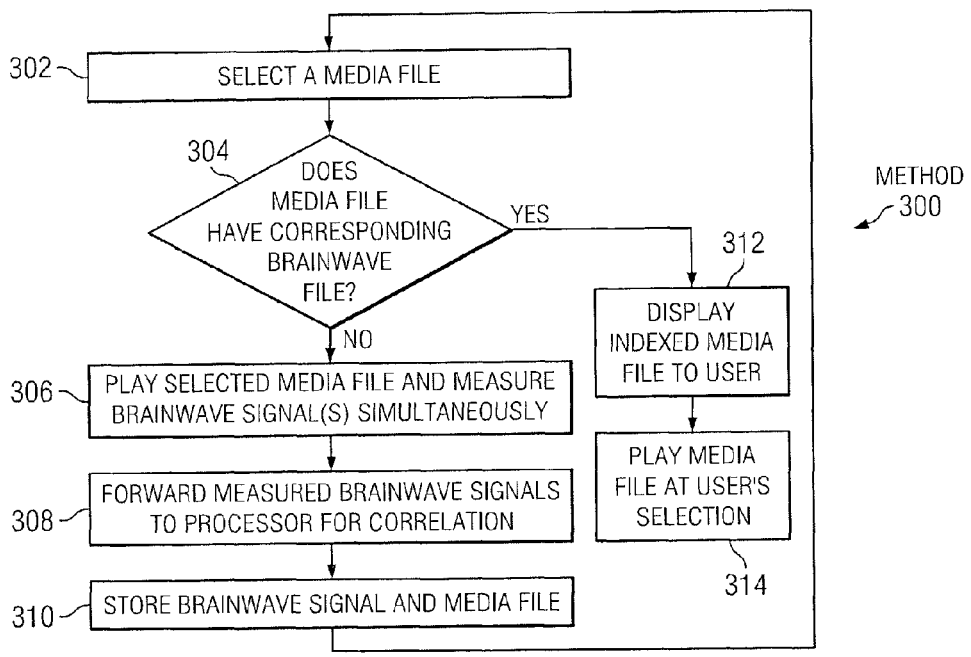
FIG. 3 illustrates an example flow chart for indexing media files and playing back an indexed media file, in accordance with particular embodiments of the present disclosure.

Preferred embodiments and their advantages are best understood by reference to FIGS. 1 through 3, wherein like numbers are used to indicate like and corresponding parts.

For purposes of this disclosure, a media file may include an audio file or a video file. In some embodiments, the media file may be a multimedia file that includes both video and audio. The media file may be transmitted over a wired and/or wireless network such as, for example, a personal area network (PAN) (e.g., BLUETOOTH), a local area network (LAN), a wide area network (WAN), a metropolitan area network (MAN), a virtual private network (VPN), an intranet, the Internet, a narrowband personal communications services (PCS) network, broadband PCS network, a circuit switched cellular network, a cellular digital packet data (CDPD) network, a radio frequency network (e.g., the 800 MHz, 900 MHz, 1.9 GHz, and 2.4 GHz bands), a satellite network, a digital or analog cable network, or any other suitable architecture or systems configured to facilitate the communication of signals, data, and/or messages. In the same or alternative embodiments, the media file may be encoded into one or more formats. Examples of encoded media files include a GPP2 multimedia file (0.3g2), a 3GPP2 multimedia file (0.3gp), an audio video interleave file (.avi), an Apple® QuickTime® movie (.mov), a MPEG-4 video file (.mp4), a MPEG video file (.mpg), a Windows® media video file (.wmv), an advanced audio coding file (.aac), MIDI file (.mid or .midi), MP3 audio file (.mp3), a MPEG-2 audio file (mpa), a WAVE audio file (.wav), and/or a Windows® media audio file (.wma).

FIG. 1 illustrates an example system 100 for indexing media files using brainwave data, in accordance with embodiments of the present disclosure. System 100 may include sensor 102, processing system 104, and media device 114.

Sensor 102 may include a sensor such as, for example, a wet electrode sensor or a dry active electrode sensor configured to detect brainwave signals of a user. An example of sensor 102 is described in U.S. Patent Publication No. 2008/0177197 by Lee et al., which has been incorporated herein by reference. In some embodiments, sensor 102 may be integrated with a headgear that can be worn by a user. Examples of headgear may include, for example, headsets, headbands, glasses, and various types of hats, helmets, caps, etc.

In one embodiment, sensor 102 may measure electroencephalogram (EEG) signals, electromyography (EMG) signals, and/or other brainwave signals when a user is playing a media file on media device 114. The brainwave signals may indicate an attention level (e.g., levels of concentration, levels of distraction, etc.) of the user while viewing and/or hearing the media file play, where the attention level may be given a value between, for example, 0 to 100, with 0 indicating the lowest level of attention and 100 being the maximum attention level. It is noted that other ranges may be assigned to determine the attention level of user. The signals measured may be subsequently processed by a processor coupled to sensor 102 (e.g., processing system 104) and based at least on the measured signal(s), the media file may be indexed. Details of the signal processing are described in more detail below with respect to processing system 104.

Processing system 104 may be coupled to sensor 102 and may include communication interface 106, processor 108, and memory 110. Communication interface 106 may include any system, device, or apparatus configured for wired and/or wireless communication with external devices, such as sensor 102, as well as various input and output (I/O) devices, for example a keyboard, a mouse, and media device 114, etc. In some embodiments, communication interface 106 may serve as an interface between processing system 104 and a network using any suitable transmission protocol and/or standard. For example, communication interface 106 may provide an interface between sensor 102 and processor 108, wherein the measured brainwave signal(s) may be forwarded to processor 108 for processing.

Processor 108 may include any system, device, or apparatus operable to interpret and/or execute program instructions and/or process data, and may include, without limitation, a microprocessor, microcontroller, digital signal processor (DSP), application specific integrated circuit (ASIC), or any other digital or analog circuitry configured to interpret and/or execute program instructions and/or process data. In some embodiments, processor 108 may receive measured brainwave signals from sensor 102 via communication interface 106 and may be configured to process the brainwave signals to quantitatively determine the mental state of the user during the playing of a media file. For example, processor 108 may correlate a user's reaction to the media file based on the brainwave signals indicating the attention level of the user (e.g., concentration, distraction, etc.). In one respect, the processor may determine one or more time intervals of the media file in which the user became distracted, indicating, for example, a funny scene or dramatic scene of the media file. Processor 108 may subsequently store the brainwave signal(s), the various time intervals of the media file where the user became distracted, and/or the media file in memory 110.

Memory 110 may be communicatively coupled to processor 108 and may include any system, device, or apparatus operable to retain program instructions (e.g., computer-readable media) or data for a period of time. Memory 110 may comprise random access memory (RAM), electrically erasable programmable read-only memory (EEPROM), a PCM-CIA card, flash memory, magnetic storage, opto-magnetic storage, or any suitable selection and/or array of volatile or non-volatile memory that retains data after power to system 104 is powered down or off. In some embodiments, memory 110 may store program instructions (e.g., management software 112), process data, brainwave signals 116, media files 118, and/or other data.

Management software 112 may include a program of instructions that, when executed by a processor, e.g., processor 108, may manage the processing of brainwave signals received from sensor 102, the playing of a media file on media device 114, the correlation of the brainwave signal and the playing media file, the time interval(s) which correspond to a user's attention level, and/or the playback of the indexed media file with the corresponding brainwave signal.

Media device 114 may be any system, device, or apparatus configured to play and/or display a media file. For example, media device 114 may be a cable and/or satellite set-top box, television, computer monitor, cellular phone, PDA, stereo, radio, gaming console, CD player, DVD player, Blu-ray player, home entertainment system, and/or other consumer electronic devices. In some embodiments, media device 114 may include a display device configured for creating graphic images and/or alphanumeric characters recognizable to a user, and may include, for example, a liquid crystal display (LCD) or a cathode ray tube (CRT). In the same or alternative embodiments, media device 114 may include speakers configured to output sound waves.

In certain embodiments, media device 114 may be communicatively coupled to or processor 104 via a wired or wireless connection. Alternatively, processor 104 may be integrated into media device 114, the combination operating as a single unit that plays and/or displays a media file while simultaneously receiving measured brainwave signals from sensor 102 via communication interface 106 and processing the received brainwave signals to determine the mental state of the user during the playing of a media file.

In operation, as a user is playing a media file on media device 114, sensor 102 may simultaneously measure brainwave signals that indicate an attention level of a user. The brainwave signals may be forwarded to processor 108 via communication interface 106, where processor 108 may index the media file. In one embodiment, processor 108 may correlate the brainwave signals and media file, and in particular, when the user was attention level indicates that the user was not fully attentive or distracted (e.g., during a dramatic or funny scene). In some embodiments, processor 104 may determine if the received brainwave signals is greater than, less than, and/or equal to a particular threshold, wherein the threshold may be a numerical value indicating a certain attention level of the user. For example, the threshold value may be a numeric value that indicates that the user is not fully attentive, e.g., distracted. Based on the comparison between the received brainwave signal and the threshold, one or more time intervals, brainwave signals, and/or some portion of or the entire the media file at which the user became distracted are stored in memory 110. When a media file is read from memory 110, if a corresponding brainwave signal exists, the corresponding brainwave signals and media file may presented to a user on media device 114, for example, as illustrated in FIGS. 2A and 2B, where the user may select one or more portions of the media file to play.

Figure 2A:
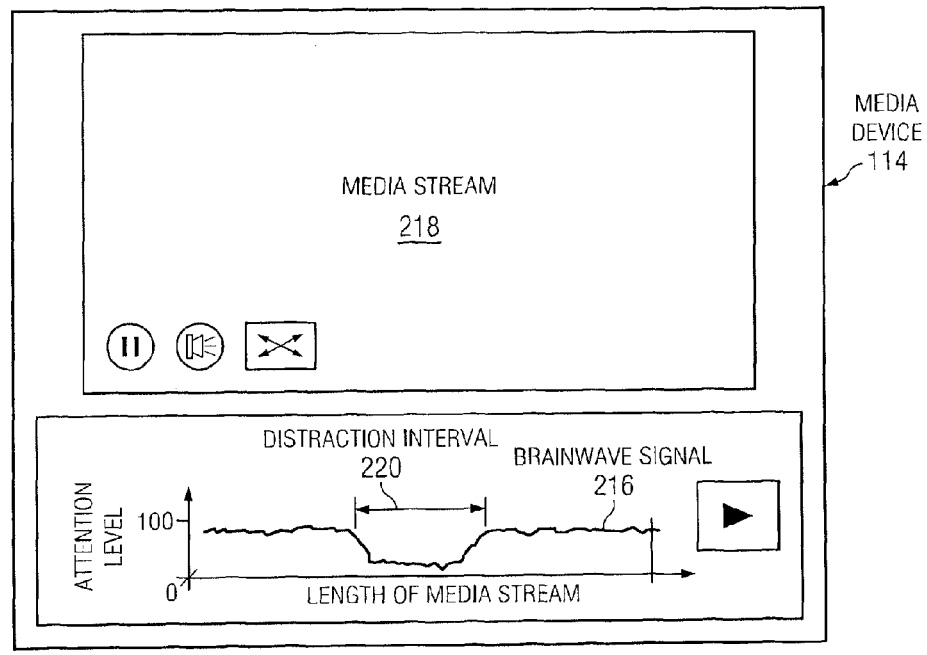
FIGS. 2A and 2B illustrate example indexed media files based on measured brainwave signals, in accordance with particular embodiments of the present disclosure.

FIG. 2A illustrates an example indexed media file with a corresponding brainwave signals, in accordance with embodiments of the present disclosure. In one embodiment, processor 108 may read media file 218 and a corresponding brainwave signal 216 from memory 110 and provide media file 218 and brainwave signal 216 to media device 114. In the same or alternative embodiments, a user may provide an indexed media file 218 to another user for playing. For example, a user may send to another user, via communication interface 106, media file 218 and corresponding brainwave signal 216 to the other user, wherein brainwave signal 216 may include one or more distraction intervals 220 indicating, for example, a portion of media file 218 that was funny or dramatic. Once media file 218 and brainwave signal 216 is received and/or opened, media device 114 may display brainwave signal 216 such that a user using an input device (e.g., keyboard, mouse, remote control, touch pad, etc.) may select where in the media file 218 to play. For example, the user may select to play media file 218 at the beginning of distraction interval 220.

Figure 2B:
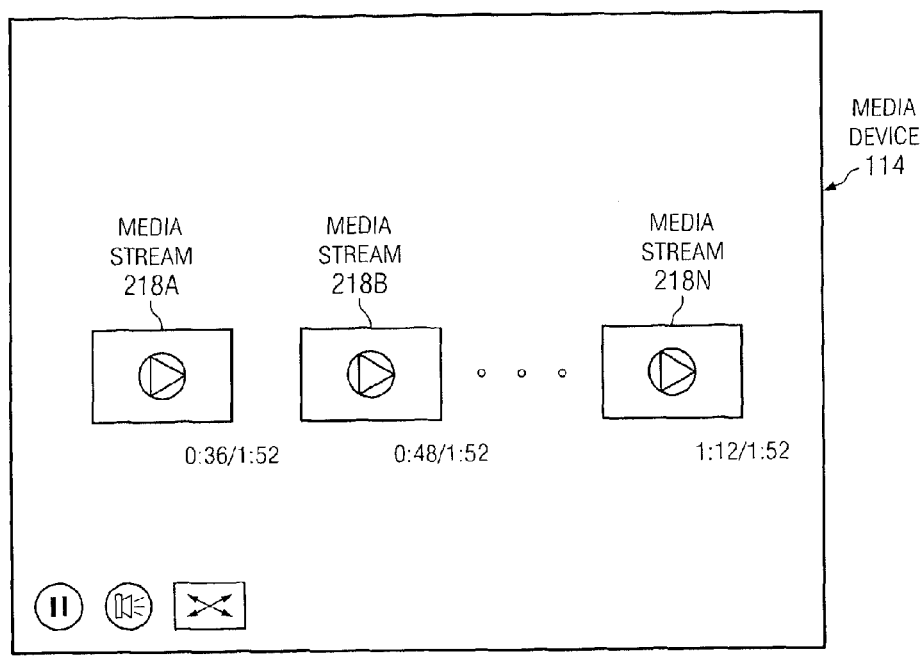

FIG. 2B illustrates another example of indexed media file 218, in accordance with certain embodiments of the present disclosure. Media device 214 may display segments of media file 218, for example, segments 218A through 218n. Segments 218 may be non-contiguous segments of the media file which correspond to a period of time in which brainwave signal indicates a user was distracted, e.g., where the brainwave signal is equal to, less than, and/or greater a threshold level. A user may select on any one of segment 218 using an input device to play on media device 214.

FIG. 3 illustrates a flow chart of an example method 300 for indexing media files and playing back an indexed media file, in accordance with embodiments of the present disclosure. At step 302, a user may select a media file. The media file may be an audio file, a video file, or a multimedia file encoded in any format and file may be communicated from any network or read from a computer-readable medium (e.g., memory 110 or memory associated with media device 114). For the purposes of this disclosure, computer-readable media may include any instrumentality or aggregation of instrumentalities that may retain data and/or instructions for a period of time. Computer-readable media may include, without limitation, storage media such as a direct access storage device (e.g., a hard disk drive or floppy disk), a sequential access storage device (e.g., a tape disk drive), compact disk, CD-ROM, DVD, random access memory (RAM), read-only memory (ROM), electrically erasable programmable read-only memory (EEPROM), and/or flash memory.

At step 304, processor 108 may determine if the selected media file includes a corresponding brainwave signal. If the media file does not have a corresponding brainwave signal, method 300 may proceed to step 306. If the media file does have a corresponding brainwave signal, method 300 may proceed to step 312 for displaying an indexed media file to the user.

At step 306, while a user is focused on a media file playing on media device 114, sensor 102 may simultaneously measure brainwave signals of the user. In some embodiments, sensor 102 may detect brainwave signals that may indicate an attention level of the user in response to the playing of the media file. The brainwave signals may be given a numerical value, e.g., between 0 to 100, wherein the lower the value, the more distracted the user is and the higher the value, the higher the concentration level.

At step 308, the measured brainwave signals may be forwarded to processor 108. In some embodiments, sensor 102 may send the measured brainwave signals, via communication interface 106 continuously as it measures the brainwave signals. In other embodiments, sensor 102 may send the signals in batches, e.g., at a predetermined time interval. Processor 108 may receive the measured brainwave signals from communication interface 106 and may correlate the measured brainwave signal to the media file. In some embodiments, processor 108 may index the media file, for example, by determining the time(s) of the media file in which the user is concentrating, is distracted, etc.

At step 310, processor 108 may forward the measured brainwave signal, the time(s) of the media file indicating various mental states of the user, and/or the media file for storing to memory 110. At any subsequent steps, if a user selects a media file that is stored in memory 110, the corresponding measured brainwave signals and/or recorded times maybe displayed on media device 114 as shown, for example, in FIGS. 2A and 2B.

At step 312, if processor 108 determines that the selected media file has a corresponding brainwave data, e.g., both stored in memory 110, processor 108 may access memory 110, retrieve the media file, the brainwave signal, and/or other data and forward the retrieve information to media device 114. Media device 114 may display the indexed media device allowing a user to select segments of the media file to play, wherein the segments may be associated with a brainwave signal greater than a particular threshold, e.g., a brainwave signal that indicates a particular attention level. In some embodiments, media device 114 may display both the media file and the brainwave signal as shown, for example, in FIG. 2A. The user may select at which point to start the media file by selecting a point along the brainwave signal (e.g., at a distraction interval). In other embodiments, media device 114 may display one or more segments of a media file corresponding to one or more distraction intervals as measured by a corresponding brainwave signal.

At step 314, based on the selection of the user, media device 114 may play the segment of media file. Once the selected segment is finished playing, media device 114 may provide the brainwave signal and/or other segments of a media file for a user to select another choice. In the same or alternative embodiment, media device 114 may allow a user to select another media file (e.g., step 302) for playing.

It is noted that while FIG. 3 discloses a particular number of steps to be taken with respect to method 300, method 300 may be executed with greater or lesser steps than those depicted in FIG. 3. In addition, although FIG. 3 discloses a certain order of steps to be taken with respect to method 300, the steps comprising method 300 may be completed in any suitable order. In addition, steps 302-314 may be repeated, independently and/or collectively, as often as desired or required by a chosen implementation.

Although the present disclosure has been described in detail, it should be understood that various changes, substitutions, and alterations may be made hereto without departing from the spirit and the scope of the invention as defined by the appended claims.

What is claimed is:

1. A method for indexing a media file, the method comprising:
receiving a selected media file;
playing the selected media file on a media device while simultaneously measuring a brainwave signal of a user with a sensor, wherein the brainwave signal indicates an attention level of the user, wherein measuring a brainwave signal comprises assigning a numeric value to the brainwave signal indicating the attention level of the user;
indexing the media file by correlating the measured brainwave signal to the media file; and
displaying one or more segments of the selected media file, each segment corresponding to correlated brainwave signal having a numeric value that exceeds a threshold value indicating a particular attention level.

2. The method according to claim 1, wherein the media file comprises an audio file, a video file, or a multimedia file.

3. The method according to claim 1, wherein indexing the played media file comprises correlating a time of the media file to the measured brainwave signal associated with that time.

4. The method according to claim 1, further comprising displaying on a media device the selected media file and a correlated brainwave signal.

5. A system for indexing media files, the system comprising:
- a media device configured to play a media file;
- a sensor configured to simultaneously measure brainwave signals of a user, wherein the brainwave signal indicates an attention level of the user, the sensor further configured to assign a numeric value to the brainwave signal indicating the attention level of the user;
- a processor coupled to the sensor and configured to receive the measured brainwave signals and index the media file by correlating the measured brainwave signal to the media file; and
- wherein the media device is further configured to display one or more segments of an indexed media file, each segment corresponding to correlated brainwave signal having a numeric value that exceeds a threshold value indicating a particular attention level.

6. The system according to claim 5, wherein the media file comprises an audio file, a video file, or a multimedia file.

7. The system according to claim 5, wherein the sensor comprises a dry active electrode sensor or a wet electrode sensor integral with a headgear worn by the user.

8. The system according to claim 5, wherein the processor is configured to correlate a time of the media file to the measured brainwave signal.

9. The system according to claim 5, wherein the media device is further configured to display an indexed media file and a brainwave signals.

10. A non-transitory computer-readable medium comprising computer-executable instructions, the instructions configured to, when executed by a processor:
- receive a selected media file;
- play the selected media file on a media device and simultaneously measure a brainwave signal of a user with a sensor, wherein the brainwave signal indicates an attention level of the user, wherein measuring a brainwave signal comprises assigning a numeric value to the brainwave signal indicating the attention level of the user;
- index the media file by correlating the measured brainwave signal to the media file; and
- display one or more segments of an indexed media file, each segment corresponding to correlated brainwave signal having a numeric value that exceeds a threshold value indicating a particular attention level.

11. The computer-readable medium according to claim 10, wherein the software is embodied in a storage device coupled to a processor of a processing system.

12. The computer-readable medium according to claim 10, wherein indexing the played media file comprises correlating a time of the media file to the measured brainwave signal.

13. The computer-readable medium according to claim 10, the instructions are further configured to display an indexed media file and a brainwave signals.

14. The computer-readable medium according to claim 10, wherein the media file comprises an audio file, a video file, or a multimedia file.

* * * * *